(12) United States Patent
Parthasaradhi Reddy et al.

(10) Patent No.: US 9,518,020 B2
(45) Date of Patent: Dec. 13, 2016

(54) PROCESS FOR REGORAFENIB

(71) Applicant: Hetero Research Foundation, Balanagar, Hyderabad (IN)

(72) Inventors: Bandi Parthasaradhi Reddy, Hyderabad (IN); Kura Rathnakar Reddy, Hyderabad (IN); Dasari Muralidhara Reddy, Hyderabad (IN); Thungathurthy Srinivasa Rao, Hyderabad (IN); Bandi Vamsi Krishna, Hyderabad (IN)

(73) Assignee: Hetero Research Foundation (IN)

( * ) Notice: Subject to any disclaimer, the term of this patent is extended or adjusted under 35 U.S.C. 154(b) by 0 days.

(21) Appl. No.: 15/026,694

(22) PCT Filed: Sep. 29, 2014

(86) PCT No.: PCT/IN2014/000630
§ 371 (c)(1),
(2) Date: Apr. 1, 2016

(87) PCT Pub. No.: WO2015/049698
PCT Pub. Date: Apr. 9, 2015

(65) Prior Publication Data
US 2016/0251313 A1   Sep. 1, 2016

(30) Foreign Application Priority Data
Oct. 4, 2013  (IN) .......................... 4511/CHE/2013

(51) Int. Cl.
*C07D 213/68* (2006.01)
*C07D 213/81* (2006.01)

(52) U.S. Cl.
CPC ......... *C07D 213/81* (2013.01); *C07B 2200/13* (2013.01)

(58) Field of Classification Search
CPC .................................................... C07D 213/68
USPC ........................................................ 546/291
See application file for complete search history.

(56) References Cited

U.S. PATENT DOCUMENTS

| | | |
|---|---|---|
| 2006/0058358 A1 | 3/2006 | Dumas et al. |
| 2010/0173953 A1* | 7/2010 | Grunenberg ......... C07D 213/81 514/350 |
| 2012/0225057 A1 | 9/2012 | Flynn et al. |
| 2013/0116442 A1 | 5/2013 | Stiehl et al. |

FOREIGN PATENT DOCUMENTS

WO    2011080749 A1    7/2011

OTHER PUBLICATIONS

International Search Report for PCT/IN2014/000630 dated Apr. 30, 2015.

* cited by examiner

*Primary Examiner* — Patricia L Morris
(74) *Attorney, Agent, or Firm* — Caesar Rivise, PC

(57) ABSTRACT

The present invention provides processes for the preparation of i) Regorafenib (4-[4-({[4-chloro-3-(trifluoromethyl)phenyl]carbamoyl}amino)-3-fluorophenoxy]-N-methylpyridine-2-carboxamide, BAY 73-4506, Stivarga®) and its pharmaceutically acceptable salt thereof; ii) a crystalline solid of Regorafenib tosylate; iii) Regorafenib Polymorph I from Regorafenib tosylate, and iv) a pure 4-(4-amino-3-fluorophenoxy)-N-methylpicolinamide from 4-amino-3-fluorophenol and 4-chloro-N-methylpicolinamide in the presence of potassium tert-butoxide.

4 Claims, 3 Drawing Sheets

PROCESS FOR REGORAFENIB

FIELD OF THE INVENTION

The present invention provides a process for the preparation of Regorafenib and its pharmaceutically acceptable salt thereof.

BACKGROUND OF THE INVENTION

Regorafenib is chemically known as 4-[4-({[4-chloro-3-(trifluoromethyl)phenyl]carbamoyl}amino)-3-fluorophenoxy]-N-methylpyridine-2-carboxamide and has the structural formula:

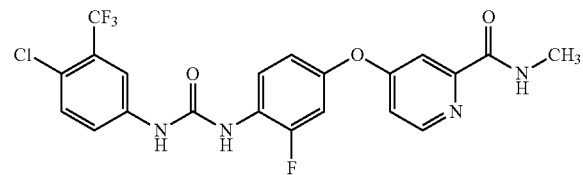 [SMILES: CNC(=O)c1cc(Oc2ccc(NC(=O)Nc3ccc(Cl)c(C(F)(F)F)c3)c(F)c2)ccn1]

Regorafenib (BAY 73-4506) is an oral multi-kinase inhibitor which targets angiogenic, stromal and oncogenic receptor tyrosine kinase (RTK). Regorafenib shows antiangiogenic activity due to its dual targeted VEGFR2-TIE2 tyrosine kinase inhibition. It is currently being studied as a potential treatment option in multiple tumor types. The generic name Regorafenib is marketed by BAYER HEALTHCARE under the brand name STIVARGA®.

Regorafenib as a compound is disclosed in U.S. Pat. No. 8,637,553. This patent application also discloses a process for the preparation of Regorafenib, which is as shown below:

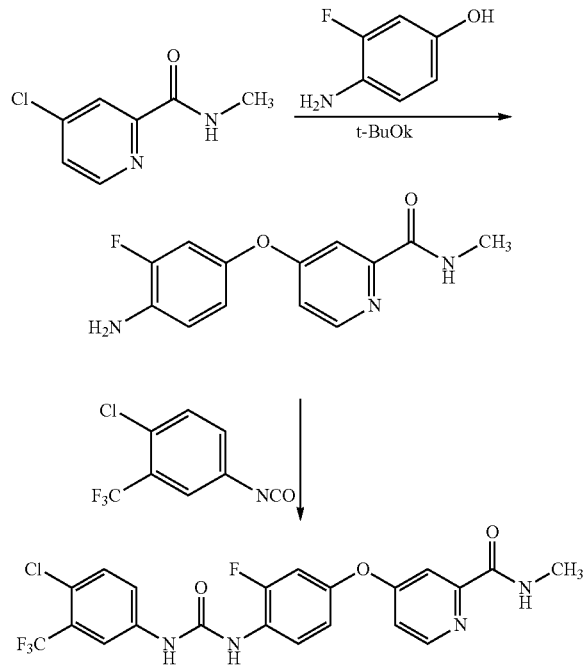

4-Amino-3-fluorophenol and 4-chloro-N- methyl-2-pyridinecarboxamide was condensed in the presence of potassium tert-butoxide, N,N-dimethylacetamide to form 4-(4-amino-3-fluorophenoxy)pyridine-2-carboxylic acid methylamide as a reddish brown solid and thereafter condensed with 4-chloro-3-(trifluoromethyl)phenyl isocyanate in toluene to form 4{4-[3-(4-chloro-3-trifluoromethylphenyl)-ureido]-3-fluorophenoxy}-pyridine-2-carboxylic acid methylamide (Regorafenib) as residue, which was triturated with diethyl ether and dried for 4 h under vacuum to obtain Regorafenib. However, the present inventors have observed that the obtained Regorafenib compound is not pure and further the trituration or column chromatography is not useful for industrial scale production.

WO 2008/043446 discloses Regorafenib polymorphic I, which is stated as obtained by following the process described in WO 2005/009961. Further this patent application also discloses monohydrate Form of Regorafenib, which is prepared by dissolving Regorafenib polymorph I in acetone or ethanol or acetonitrile or tetrahydrofuran and adding water as antisolvent.

WO 2008/055629 discloses Polymorph III of Regorafenib, which is prepared by heating Regorafenib monohydrate.

WO 2008/058644 discloses Polymorph II of Regorafenib, which is prepared by suspending Regorafenib Polymorph I in ethyl acetate by heating and thereafter cooling.

In the prior-art there is no exemplified process or described process for preparing Regorafenib polymorph I, having high purity, industrially applicable and commercially viable. The present inventors have now found a process for the preparation of Regorafenib polymorph Form I, which is industrially viable.

OBJECTIVES

The objective of the present invention is to provide a process for the preparation of 4-(4-amino-3-fluorophenoxy)-N-methylpicolinamide having purity greater than 99.4%.

Another objective of the present invention is to provide a crystalline solid of Regorafenib tosylate and a process for the preparation thereof.

Another objective of the present invention is to provide a process for the preparation of Regorafenib Polymorph I having purity greater than 99.7%.

SUMMARY OF THE INVENTION

The present invention provides a process for the preparation of 4-(4-amino-3-fluorophenoxy)-N-methylpicolinamide, having purity greater than 99.4%, which comprises:
  a) reacting the 4-amino-3-fluorophenol with 4-chloro-N-methylpicolinamide in the presence of potassium tertiary butoxide and a solvent selected from dimethyl acetamide, dimethylformamide, dimethyl sulfoxide;
  b) heating the reaction mass obtained in step (a) above 70° C.;
  c) quenching the reaction mass with an ester solvent and water;
  d) concentrating the reaction mass;
  e) adding an ether solvent to the residual mass obtained in step (d);
  f) isolating the wet solid;
  g) adding an alcohol solvent to the wet solid;
  h) heating the suspension obtained in step (g) at reflux; and
  i) isolating the 4-(4-amino-3-fluorophenoxy)-N-methylpicolinamide.

In another aspect of the present invention, provides a crystalline solid of Regorafenib tosylate.

In another aspect of the present invention provides a process for the preparation of a crystalline solid of Regorafenib tosylate, which comprises:
a) condensing 4-(4-amino-3-fluorophenoxy)-N-methylpicolinamide with 4-chloro-3-(trifluoromethyl)aniline in presence of 1,1'-carbonyldiimidazole and a chlorinated solvent;
b) removing the solvent from the reaction mass obtained in step (a) to obtain a residual mass;
c) adding p-toluenesulfonic acid to the residual mass obtained in step (b); and
d) isolating the crystalline solid of Regorafenib tosylate.

Yet in another aspect of the present invention provides a novel process for the preparation of Regorafenib Polymorph I, which comprises:
a) dissolving Regorafenib tosylate in water and an ester solvent;
b) adjusting the pH to about 9.0 to 10.0 with a base;
c) removing the solvent from the reaction mass;
d) adding a ketonic solvent to the residual solid obtained in step (c);
e) heating the suspension obtained in step (d) at reflux; and
f) isolating Regorafenib Polymorph I.

X-ray powder diffraction spectrum was measured on a bruker axs D8 advance X-ray powder diffractometer having a copper-Kα radiation. Approximately 500 mg of sample was gently flattered on a sample holder and scanned from 2 to 50 degrees two-theta, at 0.020 degrees two theta per step and a step time of 10.6 seconds. The sample was simply placed on the sample holder. The sample was rotated at 30 rpm at a voltage 40 KV and current 35 mA.

DETAILED DESCRIPTION OF THE INVENTION

The term "room temperature" refers to temperature at about 25 to 35° C.

The present invention provides a process for the preparation of 4-(4-amino-3-fluorophenoxy)-N-methylpicolinamide, having purity greater than 99.4%, which comprises, reacting the 4-amino-3-fluorophenol with 4-chloro-N-methylpicolinamide in the presence of potassium tertiary butoxide and a solvent selected from dimethyl acetamide, dimethylformamide, dimethyl sulfoxide; heating the reaction mass above 70° C.; quenching the reaction mass with an ester solvent selected from group comprising of ethyl acetate, methyl acetate, isopropyl acetate, tert-butyl acetate, ethyl formate, preferably ethyl acetate and water; concentrating the reaction mass; adding an ether solvent selected from group comprising of tetrahydrofuran, diisopropyl ether, tetrahydropyran, 1,4-dioxane, methyl tert-butyl ether, ethyl tert-butyl ether, diethyl ether, di-tert-butyl ether, diglyme, dimethoxyethane, dimethoxymethane, methoxyethane, preferably methyl tert-butyl ether; isolating the wet solid; adding an alcohol solvent selected from group comprising of methanol, ethanol, isopropyl alcohol, isobutanol, n-butanol, preferably isopropyl alcohol; heating the suspension at reflux and isolating the 4-(4-amino-3-fluorophenoxy)-N-methylpicolinamide.

Figure 1:
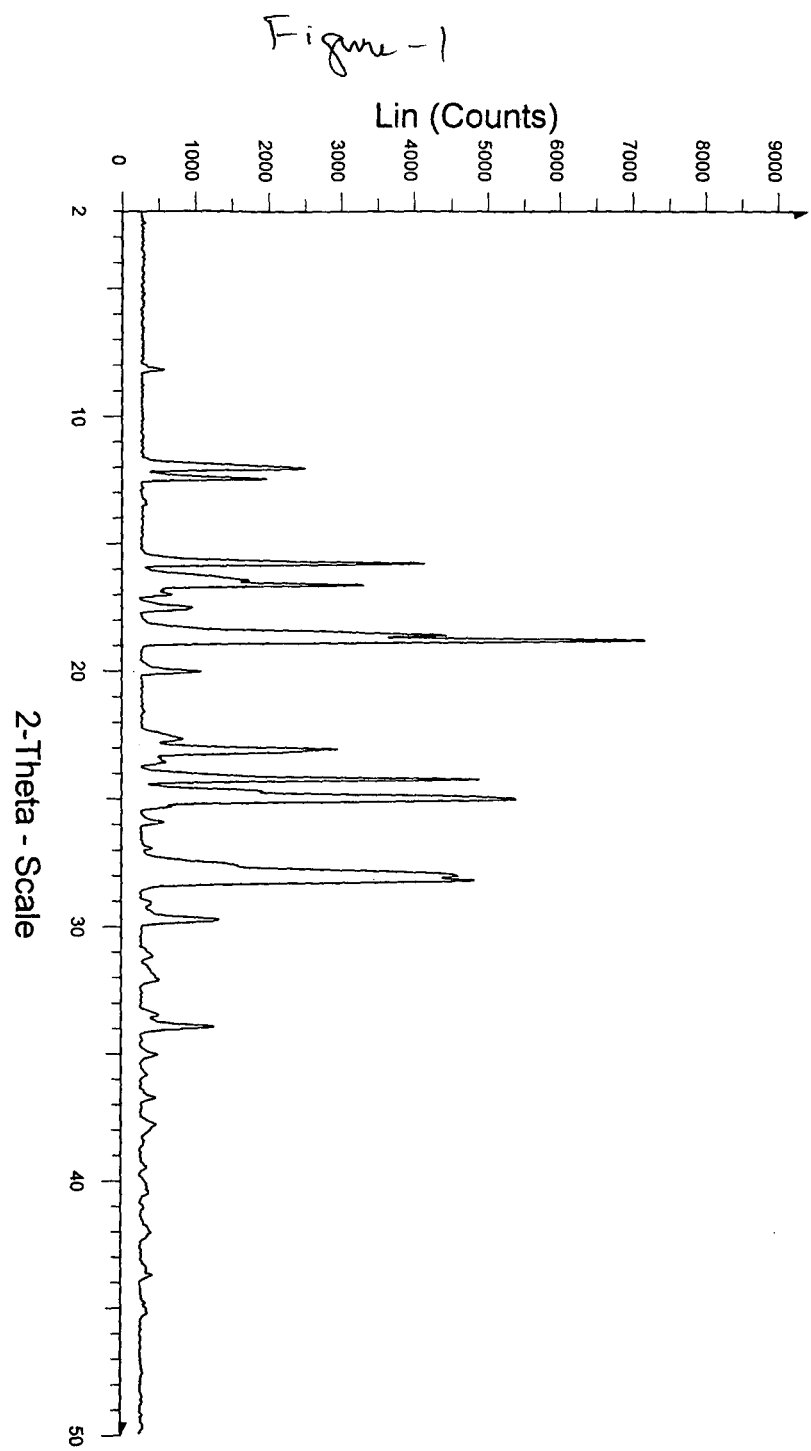
FIG. 1 is an X-ray powder diffraction spectrum of 4-(4-amino-3-fluorophenoxy)-N-methylpicolinamide.

In another aspect of the present invention, the 4-(4-amino-3-fluorophenoxy)-N-methylpicolinamide compound is isolated as crystalline compound, which is characterized having a powdered X-ray diffractogram (PXRD) as shown in FIG. 1.

The reaction mass heated above above 70° C., may preferably heated to 90 to 110° C.

Preferably the reaction mass is concentrated in by distilling off the solvent. The distilling off the solvent may be carried out at atmospheric pressure or at reduced pressure. The distillation may preferably be carried out until the solvent is almost completely distilled off.

The wet solid may be isolated by methods known such as filtration or centrifugation.

Isolation can be performed by conventional methods such as cooling, removal of solvents, concentrating the reaction mass, adding an anti-solvent, extraction with a solvent and the like.

Figure 2:
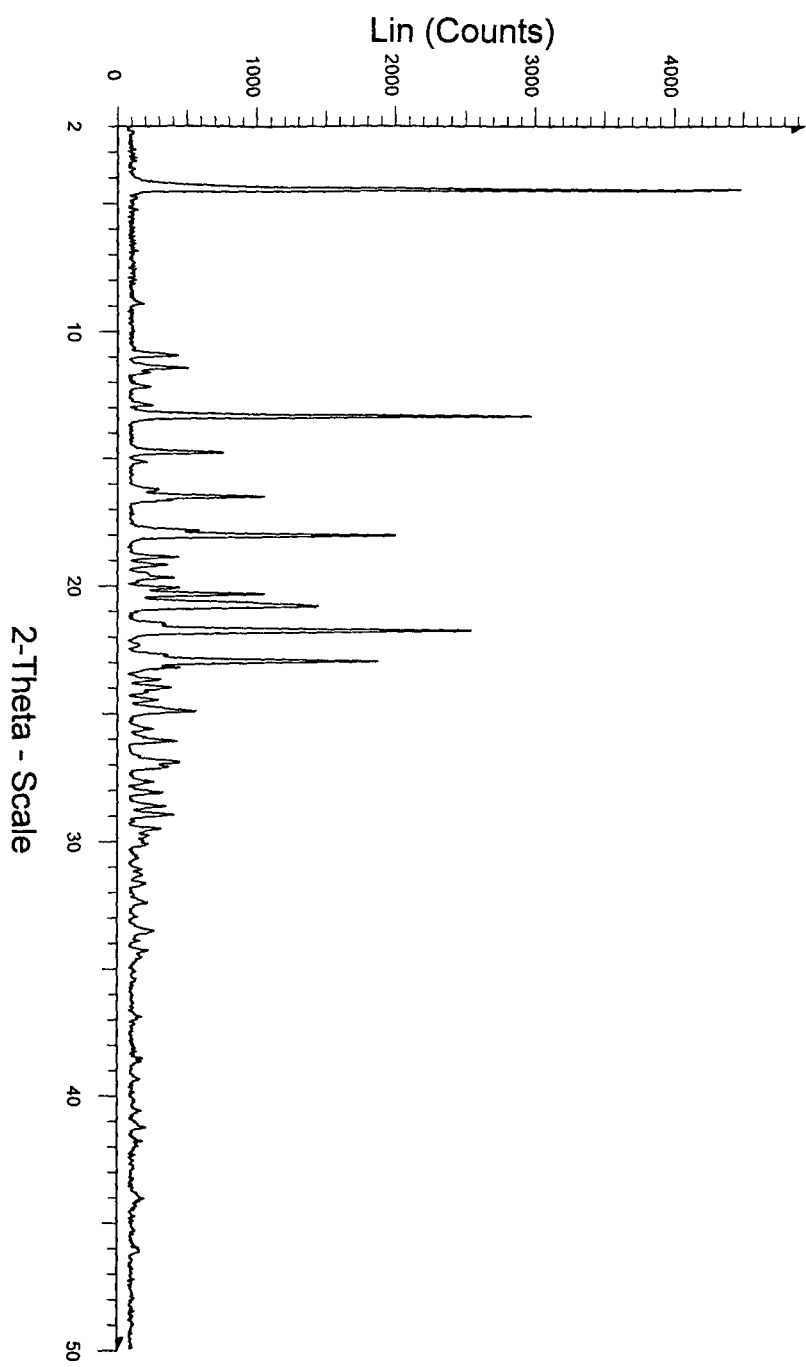
FIG. 2 is an X-ray powder diffraction spectrum of Regorafenib tosylate.
Figure 3:
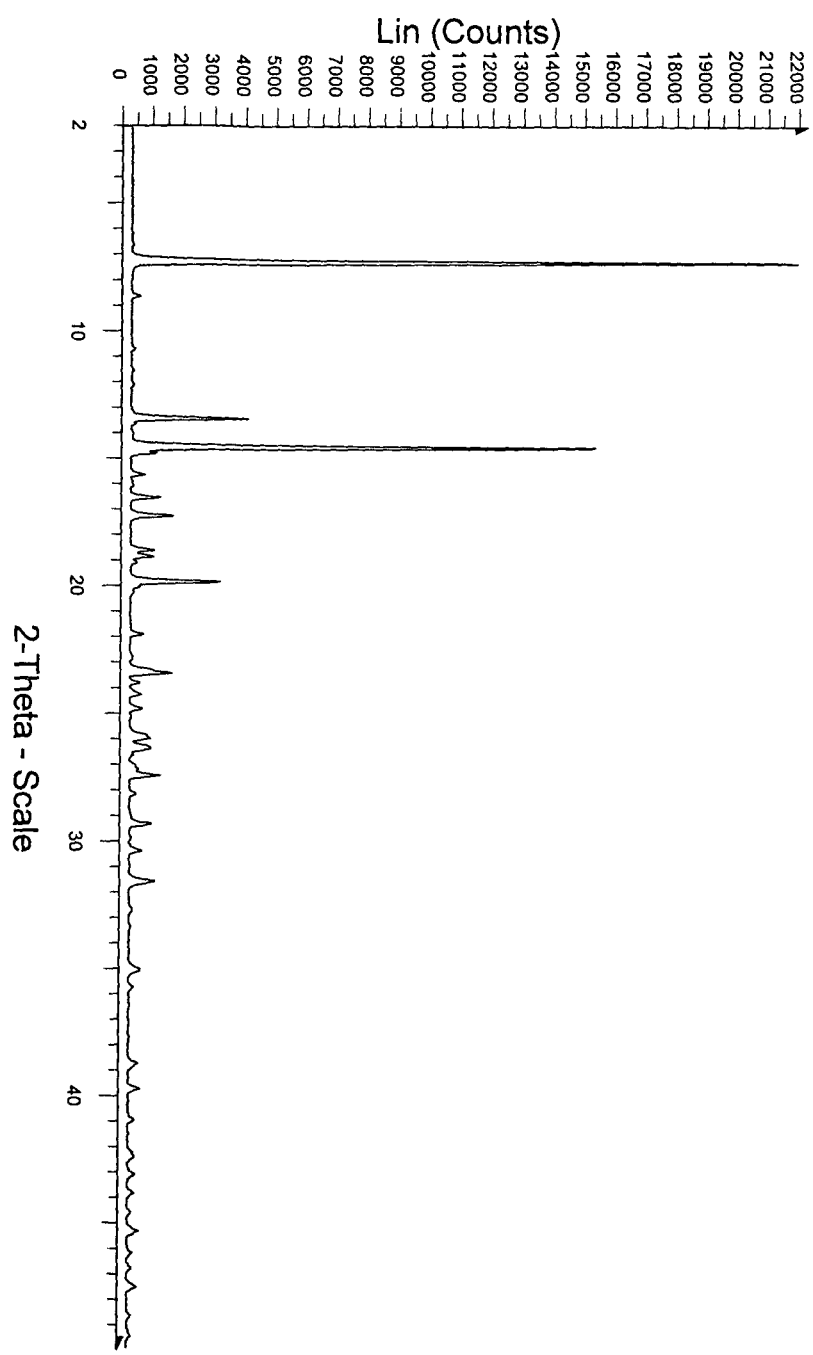
FIG. 3 is an X-ray powder diffraction spectrum of Regorafenib Polymorph I.

According to another aspect of the present invention provided a crystalline solid of Regorafenib tosylate, which is characterized by powdered X-ray diffractogram (PXRD) as shown in FIG. 2.

Another aspect of the present invention provides a process for the preparation of a crystalline solid of Regorafenib tosylate, which comprises condensing 4-(4-amino-3-fluorophenoxy)-N-methylpicolinamide with 4-chloro-3-(trifluoromethyl)aniline in presence of 1,1'-carbonyldiimidazole and a chlorinated solvent selected from group comprising of methylene chloride, ethylene dichloride, chloroform, carbon tetrachloride, preferably methylene chloride; removing the solvent to obtain a residual mass; adding p-toluenesulfonic acid and isolating the crystalline solid of Regorafenib tosylate.

Removal of the solvent may be carried out at atmospheric pressure or at reduced pressure. Removal of the solvent may preferably be carried out until the solvent is almost completely distilled off.

The crystalline solid of Regorafenib tosylate may be isolated by methods known such as filtration or centrifugation.

Yet another aspect of the present invention provides a novel process for the preparation of Regorafenib Polymorph I, which comprises dissolving Regorafenib tosylate in water and an ester solvent selected from group comprising of ethyl acetate, methyl acetate, isopropyl acetate, tert-butyl acetate, ethyl formate; preferably ethyl acetate; adjusting the pH to about 9.0 to 10.0 with a base selected from group comprising of sodium carbonate, sodium hydroxide, sodium bicarbonate, potassium hydroxide, potassium carbonate, potassium bicarbonate, cesium carbonate, cesium bicarbonate, calcium carbonate, calcium bicarbonate, preferably sodium hydroxide; removing the solvent from the reaction mass; adding a ketonic solvent selected from group comprising of acetone, diethyl ketone, methyl ethyl ketone, methyl, propyl ketone, methyl isobutyl ketone, methyl tert-butyl ketone, preferably acetone to the residual solid; heating the suspension at reflux and isolating Regorafenib Polymorph I.

Removal of the solvent may be carried out in step (c) at atmospheric pressure or at reduced pressure. Removal of the solvent may preferably be carried out until the solvent is almost completely distilled off.

Regorafenib Polymorph I may be isolated by methods known such as filtration or centrifugation.

The invention will now be further described by the following example, which is illustrative rather than limiting.

EXAMPLES

Example 1

Preparation of 4-(4-amino-3-fluorophenoxy)-N-methylpicolinamide

4-Amino-3-fluorophenol (50 gm) was dissolved in dimethylacetamide (500 ml) and cooled to 0 to 5° C. The solution was stirred for 15 minutes and potassium tertiary butoxide (50 gm) was added to the solution slowly at 0 to 5° C. The reaction mixture was stirred for 45 minutes at 0 to 5° C. and a solution of 4-chloro-N-methylpicolinamide (52 gm) in dimethylacetamide (200 ml) was added to the reaction mixture slowly for 20 minutes at 0 to 5° C. The contents were heated to 100° C. and stirred for 11 hours. The reaction mass was then cooled to room temperature and quenched with water (1500 ml) and ethyl acetate (1500 ml). The layers were separated and aqueous layer was extracted with ethyl acetate. Combined organic layers were dried with sodium sulfate and subject to carbon. Thereafter the carbon was removed through hyflow and the solvent was distilled off from the organic layer under vacuum below 55° C. to obtain the title compound as residual solid.
Chromatographic Purity (by HPLC)—89.5%

Example 2

To the residual solid obtained in Example 1 was added methyl tert-butyl ether (200 ml) at room temperature, stirred for 2 hours and filtered. To the wet solid thus obtained was added isopropyl alcohol (180 ml) at room temperature and heated to reflux. The solution was stirred for 1 hour at reflux and then cooled to 10 to 15° C. The contents were stirred for 1 hour at 10 to 15° C. and filtered. The solid obtained was dried to obtain 54 gm of 4-(4-amino-3-fluorophenoxy)-N-methylpicolinamide.
Chromatographic Purity (by HPLC)—97.4%

Example 3

Preparation of Regorafenib tosylate

A mixture of 4-chloro-3-(trifluoromethyl)aniline (80 gm), 1,1'-carbonyldiimidazole (71 gm) and methylene chloride (640 ml) were added at room temperature and stirred for 19 hours. To the reaction mixture was added a solution of 4-(4-amino-3-fluorophenoxy)-N-methylpicolinamide (50 gm) in methylene chloride (500 ml) slowly at room temperature and stirred for 36 hours. The layers were separated and the aqueous layer was extracted with methylene chloride. Combined organic layers were dried with sodium sulfate and subject to carbon. Thereafter the carbon was removed through hyflow and solvent was distilled off from the organic layer under vacuum below 55° C. to obtain a residual mass. The residual mass thus obtained was cooled to room temperature and p-toluenesulfonic acid (33 gm) was added. The reaction mass was cooled to 10° C. and stirred for 1 hour. The solid obtained was collected by filtration and then dried to obtain 68 gm of Regorafenib tosylate.
Chromatographic Purity (by HPLC)—97.8%

Example 4

Preparation of Regorafenib Polymorph I

Regorafenib tosylate was dissolved in ethyl acetate and water at room temperature and then heated to 55° C. The pH of the solution was adjusted to 9.0 to 10.0 with sodium hydroxide solution at 55 to 60° C. The layers were separated and the aqueous layer was extracted with ethyl acetate. Combined organic layers were dried with sodium sulfate and then concentrated to obtain a residual solid. To the residual solid was added acetone and heated to reflux. The solution was stirred for 1 hour at reflux and then cooled to 5° C. The contents were stirred for 1 hour at 5° C. and filtered. The solid obtained was dried to obtain 33 gm of Regorafenib Polymorph I.
Chromatographic Purity (by HPLC)—99.7%

Example 5

Preparation of Regorafenib Polymorph I

Regorafenib tosylate was dissolved in ethyl acetate and water at room temperature and then heated to 55° C. The pH of the solution was adjusted to 9.0 to 10.0 with sodium hydroxide solution at 55 to 60° C. The layers were separated and the aqueous layer was extracted with ethyl acetate. Combined organic layers were dried with sodium sulfate and then concentrated to obtain a residual solid. To the residual solid was added methyl ethyl ketone and heated to reflux. The solution was stirred for 1 hour at reflux and then cooled to 5° C. The contents were stirred for 1 hour at 5° C. and filtered. The solid obtained was dried to obtain 33 gm of Regorafenib Polymorph I.
Chromatographic Purity (by HPLC)—99.7%

We claim:

1. A process for the preparation of Regorafenib Polymorph I, which comprises:
    a) dissolving Regorafenib tosylate in water and an ester solvent;
    b) adjusting the pH to about 9.0 to 10.0 with a base;
    c) removing the solvent from the reaction mass;
    d) adding a ketonic solvent to the residual solid obtained in step (c);
    e) heating the suspension obtained in step (d) at reflux; and
    f) isolating Regorafenib Polymorph I.

2. The process according to claim 1, wherein the ester solvent used in step (a) is selected from group comprising of ethyl acetate, methyl acetate, isopropyl acetate, tert-butyl acetate and ethyl formate.

3. The process according to claim 1, wherein the base used in step (b) is selected from group comprising of sodium carbonate, sodium hydroxide, sodium bicarbonate, potassium hydroxide, potassium carbonate, potassium bicarbonate, cesium carbonate, cesium bicarbonate, calcium carbonate and calcium bicarbonate.

4. The process according to claim 1, wherein the ketonic solvent used in step (d) is selected from group comprising of acetone, diethyl ketone, methyl ethyl ketone, methyl propyl ketone, methyl isobutyl ketone and methyl tert-butyl ketone.

* * * * *